(12) United States Patent
Takano et al.

(10) Patent No.: US 8,410,308 B2
(45) Date of Patent: Apr. 2, 2013

(54) PROCESS FOR PRODUCTION OF OXYGEN-CONTAINING ORGANIC COMPOUND

(75) Inventors: Minoru Takano, Himeji (JP); Naruhisa Hirai, Himeji (JP); Yasutaka Ishii, Takatsuki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 154 days.

(21) Appl. No.: 12/919,494

(22) PCT Filed: Feb. 27, 2009

(86) PCT No.: PCT/JP2009/000892
§ 371 (c)(1),
(2), (4) Date: Aug. 26, 2010

(87) PCT Pub. No.: WO2009/110203
PCT Pub. Date: Sep. 11, 2009

(65) Prior Publication Data
US 2010/0331569 A1  Dec. 30, 2010

(30) Foreign Application Priority Data
Mar. 4, 2008 (JP) ................... 2008-053296

(51) Int. Cl.
*C07C 51/50* (2006.01)
(52) U.S. Cl. ...................................... 562/417
(58) Field of Classification Search ........... None
See application file for complete search history.

(56) References Cited

FOREIGN PATENT DOCUMENTS

| | | | |
|---|---|---|---|
| JP | 8-38909 A | 2/1996 | |
| JP | 2001-253838 A | 9/2001 | |
| JP | 2005-034707 A | 2/2005 | |
| JP | 2005-118718 A | 5/2005 | |

OTHER PUBLICATIONS

International Search Report—dated Apr. 28, 2009 for PCT/JP2009/000892.
Shokubai, vol. 42, No. 2, 2000, pp. 100-102.
Shokubai, vol. 48, No. 1, 2006, pp. 2-8.

*Primary Examiner* — Kamal Saeed
(74) *Attorney, Agent, or Firm* — Birch, Stewart, Kolasch & Birch, LLP

(57) ABSTRACT

Disclosed is a process for the production of an oxygen-containing organic compound by oxidizing an organic compound with molecular oxygen in a liquid phase in the presence both of a catalytic nitrogen-containing cyclic compound and a catalyst including a solid superacid and, supported thereon, a transition metal compound, in which the nitrogen-containing cyclic compound contains, as a ring constituent, a skeleton represented by following Formula (1), wherein X represents an —OR group, and wherein R represents hydrogen atom or a hydroxyl-protecting group. The process gives the oxygen-containing organic compound in a high yield and enables easy recovery and reuse of the catalyst.

[Chemical Formula 1]

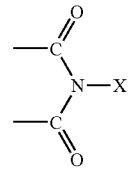

(1)

7 Claims, No Drawings

PROCESS FOR PRODUCTION OF OXYGEN-CONTAINING ORGANIC COMPOUND

TECHNICAL FIELD

The present invention relates to a process for oxidizing organic compounds with molecular oxygen to produce oxygen-containing organic compounds such as carboxylic acids, aldehydes, ketones, and alcohols. Such oxygen-containing organic compounds are useful in the chemical industry.

BACKGROUND ART

By the catalyses both of a nitrogen-containing cyclic compound and of a transition metal compound (represented by cobalt or manganese), organic compounds are oxidized with molecular oxygen to give oxygen-containing organic compounds. In an exemplary known production process of this type, the transition metal compound is dissolved in a reaction solution when used (Patent Document 1). The transition metal compounds form a relatively large proportion of the production cost. A possible solution to reduce the production cost is reduction of the amount of the transition metal compounds, but the reduction of the amount causes problems such as a lower yield and is impractical.

A strong demand has therefore been made to recover and reuse transition metal compounds after use. However, it is generally difficult to recover such transition metal compounds dissolved in reaction solutions. A possible solution to easy recovery of a transition metal compound is allowing the transition metal compound to be supported on a support before use, and recovering the transition metal compound as being supported on the support after use. However, even when the support is recovered, the transition metal compound is not efficiently recovered, because the transition metal compound is dissolved out or eluted into the reaction solution during a reaction process between an organic compound and molecular oxygen. Accordingly, there has not yet been actually found a process for the production of an oxygen-containing organic compound by oxidizing an organic compound with molecular oxygen to give the oxygen-containing organic compound in a high yield, in which a transition metal compound used as a catalyst is easily recoverable and reusable.

Patent Document 1: Japanese Unexamined Patent Application Publication (JP-A) No. 2001-253838

DISCLOSURE OF INVENTION

Problems to be Solved by the Invention

Accordingly, an object of the present invention is to provide a process for the production of an oxygen-containing organic compound by oxidizing an organic compound with molecular oxygen, which process uses a transition metal compound that is easily recoverable and reusable and has such excellent catalytic potency as to synthetically produce an oxygen-containing organic compound in a high yield even after repeated uses.

Means for Solving the Problems

After intensive investigations to achieve the object, the present inventors have found that use of a solid superacid as a support for a transition metal compound inhibits the transition metal compound to be eluted into the reaction solution during production processes of an oxygen-containing organic compound and that the transition metal compound supported on the solid superacid support can be easily and efficiently recovered and reused by recovering the support. They have also found that the transition metal compound supported on the solid superacid, when used in combination with a nitrogen-containing cyclic compound, shows excellent catalytic potency with respect to the reaction between the organic compound and molecular oxygen to give an oxygen-containing organic compound in a high yield even after repeated use-recovery procedures. The present invention has been made based on these findings and further investigations.

Specifically, the present invention provides a process for the production of an oxygen-containing organic compound. The process includes the step of oxidizing an organic compound with molecular oxygen in a liquid phase in the presence both of a nitrogen-containing cyclic compound and of a catalyst including a solid superacid and, supported thereon, a transition metal compound, to give the oxygen-containing organic compound, the nitrogen-containing cyclic compound containing, as a ring constituent, a skeleton represented by following Formula (1):

[Chemical Formula 1]

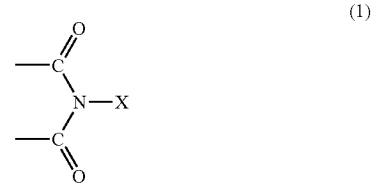

wherein X represents an —OR group, wherein R represents a hydrogen atom or a hydroxyl-protecting group.

The solid superacid is preferably a sulfated zirconia.

The transition metal compound is preferably a cobalt compound and/or a manganese compound.

Advantages

The process for the production of an oxygen-containing organic compound, according to the present invention, uses a catalytic transition metal compound supported on a solid superacid, whereby the transition metal compound can be easily and efficiently recovered by recovering the solid superacid, and the recovered transition metal compound can be reused. The process enables significant reduction of production cost of oxygen-containing organic compounds and thereby enables inexpensive production of oxygen-containing organic compounds which are useful in the chemical industry, because the transition metal compound, which forms a large proportion of the production cost, can be recovered and reused and, even after repeating use-recovery procedures multiple times, shows little deterioration in catalytic potency. As used herein the term "transition metal compound" also includes a salt of a transition metal.

BEST MODES FOR CARRYING OUT THE INVENTION

Catalysts

A feature of the present invention is the use of a solid superacid as a support (carrier) for supporting a transition metal compound. The "solid superacid" is defined as an acid having an acid strength stronger than that of 100% sulfuric acid ("Superacids and Superbases (in Japanese)" by Kozo Tanabe and Ryoji Noyori, Kodansha (1980)) and is an acid having a Hammett acidity function ($H_0$) of less than −11.93.

Exemplary solid superacids include immobilized liquid superacids prepared typically by allowing a solid (e.g., $Al_2O_3$, $SiO_2$, zeolite, $SiO_2$—$Al_2O_3$, a polymer, graphite, or a metal) to carry a liquid superacid (e.g., $SbF_5$, $BF_3$, $BF$—$SbF_5$, $FSO_3H$—$SbF_5$, or $TaF_5$); binary metal salts prepared by grinding and mixing $AlCl_3$ or $AlBr_3$ with another component such as $CuSO_4$, $CuCl_2$, $Ti_2(SO_4)_3$, or $TiCl_3$; sulfated metal oxides prepared by allowing a metal oxide (e.g., $Fe_2O_3$, $TiO_2$, $ZrO_2$, $HfO_2$, $SnO_2$, $Al_2O_3$, or $SiO_2$) to adsorb sulfate ion and firing the resulting article to give the metal oxide carrying the sulfate ion bound thereto; noble metal/sulfated metal oxides prepared by adding a noble metal (e.g., Ir or Pt) to any of the sulfated metal oxides; metal oxide superacids prepared by allowing a metal oxide (e.g., $ZrO_2$, $SnO_2$, $TiO_2$, or $Fe_2O_3$) to adsorb, for example, $WO_3$, $MoO_3$, or $B_2O_3$ and firing the resulting article at high temperatures; superacidic ion-exchange resins including nonporous or porous ion-exchange resins having a superacid group such as —$CF_2CF_2SO_3H$ (e.g., fluorinated sulfonic acid resins "Nafion NR50" (supplied by Aldrich (now part of Sigma-Aldrich Corporation)) and "Nafion H" (supplied by E.I. du Pont de Nemours & Company); and heteropolyacids including polyacids having an element such as P, Mo, V, W, or Si.

Of solid superacids for use herein, preferred are sulfated metal oxides, noble metal/sulfated metal oxides, and metal oxide superacids, of which sulfated metal oxides and noble metal/sulfated metal oxides are more preferred. Such sulfated metal oxides and noble metal/sulfated metal oxides have particularly high acid strengths, have Hammett acidity functions ($H_0$) of less than −16, and can thereby support transition metal compounds more effectively. Exemplary preferred sulfated metal oxides include sulfated zirconia, sulfated tin oxide, and sulfated hafnium oxide; and exemplary preferred noble metal/sulfated metal oxides include Pt/sulfated zirconia, Ir/sulfated zirconia, and Pd/sulfated zirconia. Among them, sulfated zirconia is industrially easily available and is thereby advantageously used herein.

In the preparation of the sulfated metal oxides and noble metal/sulfated metal oxides, the way to allow the carrier (support) to carry a compound to be supported is not especially limited and can be chosen from among known or common processes.

The shape and particle size of the carrier (support) are not critical and can be chosen as an appropriate shape and particle size suitable for an apparatus used in the recovery of the catalyst. For example, the support can have such a shape generally adopted as a solid catalyst, such as a pellet or powder shape.

Though not limited, a metal element constituting the transition metal compound to be supported on the solid superacid is often a metal element belonging to Groups 3 to 12 of the periodic table. Examples of the metal element include, of the periodic table, Group 3 elements such as Sc, lanthanoid elements, and actinoid element; Group 4 elements such as Ti, Zr, and Hf; Group 5 elements such as V; Group 6 elements such as Cr, Mo, and W; Group 7 elements such as Mn; Group 8 elements such as Fe and Ru; Group 9 elements such as Co and Rh; Group 10 elements such as Ni, Pd, and Pt; Group 11 elements such as Cu; and Group 12 elements such as Zn. Preferred metal elements include elements belonging to Groups 5 to 11 of the periodic table, of which elements belonging to Groups 5 to 9, such as Co, Mn, Fe, V, and Mo, are more preferred. The valence of the metal element is not critical and can be about 0 to 6.

Exemplary transition metal compounds include, of the metal elements, inorganic compounds and organic compounds. Exemplary inorganic compounds include elementary substances; hydroxides; oxides (including multicomponent oxides); halides such as fluorides, chlorides, bromides, and iodides; salts of oxoacids, such as nitrates, sulfates, phosphates, borates, and carbonates; salts of isopolyacids; and salts of heteropolyacids. Exemplary organic compounds include acetates, propionates, prussiates (cyanides), naphthenates, stearates, and other salts of organic acids; methanesulfonates, ethanesulfonates, octanesulfonates, dodecanesulfonates, and other salts of alkyl-substituted sulfonic acids (e.g., alkyl-sulfonates whose alkyl moiety having 1 to 18 carbon atoms); benzenesulfonates, p-toluenesulfonates, naphthalenesulfonates, decylbenzenesulfonates, dodecylbenzenesulfonates, and other salts of aryl-substituted sulfonic acids whose aryl moiety may be substituted with an alkyl group (e.g., alkyl-arylsulfonates whose alkyl moiety having 6 to 18 carbon atoms); and complexes. Exemplary ligands for constituting the complexes include OH (hydroxo), alkoxys (e.g., methoxy, ethoxy, propoxy, and butoxy), acyls (e.g., acetyl and propionyl), alkoxycarbonyls (e.g., methoxycarbonyl and ethoxycarbonyl), acetylacetonato, cyclopentadienyl group, halogen atoms (e.g., chlorine and bromine), CO, CN, oxygen atom, $H_2O$ (aquo); phosphorus compounds including phosphines (e.g., triarylphosphines such as triphenylphosphine); and nitrogen-containing compounds such as $NH_3$ (amine), NO, $NO_2$ (nitro), $NO_3$ (nitrato), ethylenediamine, diethylenetriamine, pyridine, and phenanthroline.

Specific examples of the transition metal compounds include, taking cobalt compounds as an example, bivalent or trivalent cobalt compounds including inorganic cobalt compounds such as cobalt hydroxide, cobalt oxide, cobalt chloride, cobalt bromide, cobalt nitrate, cobalt sulfate, and cobalt phosphate; salts of organic acids, such as cobalt acetate, cobalt naphthenate, and cobalt stearate; and complexes such as cobalt acetylacetonate. Independently, specific examples of manganese compounds include bivalent, trivalent, tetravalent, or pentavalent manganese compounds including inorganic compounds such as manganese hydroxide, manganese oxide, manganese chloride, and manganese sulfate; and complexes such as manganese acetylacetonate. Exemplary compounds of other transition metal elements include compounds corresponding to the cobalt or manganese compounds. Each of different transition metal compounds can be used alone or in combination. A combination use of two or more transition metal compounds having different valences (e.g., a bivalent metallic compound and a trivalent metallic compound) is also preferred. As the transition metal compound for use in the present invention, compounds having at least one of Co, Mn, Fe, Zr, Ce, V, and Mo as the transition metal are preferred. Among them, cobalt compounds and manganese compounds are more preferred, of which cobalt and manganese salts of organic acids are further preferred. Above all, the combination use of one or more cobalt compounds with one or more manganese compounds is especially preferred to prevent the catalyst from reduction in activity.

The transition metal compounds can be supported on the solid superacid according to a common procedure such as impregnation, firing, precipitation, and ion exchange. The amount of the transition metal compounds to be supported is, in terms of metal atoms in the transition metal compounds, typically about 0.001 to 20 percent by weight, preferably about 0.01 to 20 percent by weight, and especially preferably about 0.1 to 10 percent by weight, relative to the amount of the solid superacid.

Another feature of the process for the production of an oxygen-containing organic compound according to the present invention is the combination use of a nitrogen-containing cyclic compound with the transition metal compound supported on the solid superacid as catalysts, in which the nitrogen-containing cyclic compound has a skeleton represented by Formula (1) as a ring constituent. The use of the nitrogen-containing cyclic compound containing the skeleton represented by Formula (1) as a ring constituent can further promote the reaction to proceed.

In Formula (1), the bond between nitrogen atom and X is either single bond or double bond. X represents an —OR group, wherein R represents a hydrogen atom or a hydroxyl-protecting group. The nitrogen-containing cyclic compound may have two or more skeletons represented by Formula (1) per molecule. When X is an —OR group and R is a hydroxyl-protecting group, the nitrogen-containing cyclic compound may have two or more of the other moiety, than R, of the skeleton represented by Formula (1), wherein X is an —OR group, being bound to each other through R.

In Formula (1), the hydroxyl-protecting group represented by R can be any of hydroxyl-protecting groups commonly used in organic synthesis. Examples of such protecting groups include alkyl groups (e.g., alkyl groups having 1 to 4 carbon atoms, such as methyl and t-butyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); groups capable of forming an acetal or hemiacetal group with hydroxyl group(s), including substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, and 1-hydroxyalkyl groups (e.g., 1-hydroxyethyl, 1-hydroxyhexyl, 1-hydroxydecyl, 1-hydroxyhexadecyl, and 1-hydroxy-1-phenylmethyl groups); acyl groups (including aliphatic saturated or unsaturated acyl groups, e.g., aliphatic acyl groups having 1 to 20 carbon atoms, such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl groups; acetoacetyl group; alicyclic acyl groups including cycloalkanecarbonyl groups such as cyclopentanecarbonyl and cyclohexanecarbonyl groups; and aromatic acyl groups such as benzoyl and naphthoyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., alkoxy-carbonyl groups whose alkoxy moiety having 1 to 4 carbon atoms, such as methoxycarbonyl, ethoxycarbonyl, and t-butoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), groups corresponding to inorganic acids (e.g., sulfuric acid, nitric acid, phosphoric acid, and boric acid), except for removing hydroxyl group (OH group) therefrom, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is an —OR group, and two or more of the other moiety, than R, of the skeleton represented by Formula (1) are bound to each other through R, examples of R include acyl groups of polycarboxylic acids, such as oxalyl, malonyl, succinyl, glutaryl, phthaloyl, isophthaloyl, and terephthaloyl groups; carbonyl group; and multivalent hydrocarbon groups such as methylene, ethylidene, isopropylidene, cyclopentylidene, cyclohexylidene, and benzylidene groups (of which groups that form an acetal bond with two hydroxyl groups are preferred).

Preferred examples of R include hydrogen atom; groups capable of forming an acetal or hemiacetal group with hydroxyl group(s); groups corresponding to acids (e.g., carboxylic acids, sulfonic acids, carbonic acid, carbamic acid, sulfuric acid, phosphoric acid, and boric acid), except for removing hydroxyl group therefrom, such as acyl groups, sulfonyl groups, alkoxycarbonyl groups, and carbamoyl groups, and other hydrolyzable protecting groups capable of being removed (deprotected) through hydrolysis. R is especially preferably hydrogen atom.

Exemplary nitrogen-containing cyclic compounds containing the skeleton represented by Formula (1) as a ring constituent include:

cyclic imide compounds each represented by following Formula (2):

[Chemical Formula 2]

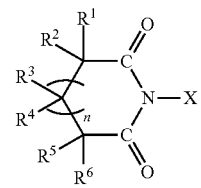

(2)

wherein "n" denotes 0 or 1; X represents an —OR group, wherein R represents a hydrogen atom or a hydroxyl-protecting group; $R^1$, $R^2$, $R^3$, $R^4$, $R^5$ and $R^6$ are the same as or different from one another and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group, wherein at least two of $R^1$, $R^2$, $R^3$, $R^4$, $R^5$, and $R^6$ may be bound to each other to form a double bond, or an aromatic or nonaromatic ring together with a carbon atom or carbon-carbon bond constituting the cyclic imide skeleton, and wherein one or more of an N-substituted cyclic imide group represented by following Formula (a):

[Chemical Formula 3]

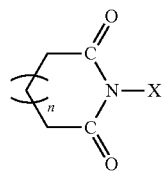

(a)

wherein "n" and X are as defined above, may further be formed on the substituents $R^1$, $R^2$, $R^3$, $R^4$, $R^5$, and $R^6$, or on the double bond or aromatic or nonaromatic ring formed by at least two of $R^1$, $R^2$, $R^3$, $R^4$, $R^5$, and $R^6$.

As the substituents $R^1$, $R^2$, $R^3$, $R^4$, $R^5$ and $R^6$ in the cyclic imide compounds represented by Formula (2), exemplary halogen atoms include iodine, bromine, chlorine, and fluorine atoms. Exemplary alkyl groups include linear or branched-chain alkyl groups having 1 to 30 carbon atoms, such as methyl, ethyl, propyl, isopropyl, butyl, hexyl, decyl, and dodecyl groups, of which those having about 1 to 20 carbon atoms are preferred.

Exemplary aryl groups include phenyl, tolyl, xylyl, and naphthyl groups; and exemplary cycloalkyl groups include cyclopentyl and cyclohexyl groups. Exemplary alkoxy groups include alkoxy groups having 1 to 30 carbon atoms, such as methoxy, ethoxy, isopropoxy, butoxy, t-butoxy, hexyloxy, decyloxy, and dodecyloxy groups, of which those having about 1 to 20 carbon atoms are preferred.

Exemplary substituted oxycarbonyl groups include alkoxy-carbonyl groups whose alkoxy moiety having 1 to 30 carbon atoms, such as methoxycarbonyl, ethoxycarbonyl, isopropoxycarbonyl, butoxycarbonyl, t-butoxycarbonyl, hexyloxycarbonyl, and decyloxycarbonyl groups, of which alkoxy-carbonyl groups whose alkoxy moiety having 1 to 20 carbon atoms are preferred; cycloalkyloxycarbonyl groups such as cyclopentyloxycarbonyl and cyclohexyloxycarbonyl groups, of which 3- to 20-membered cycloalkyloxycarbonyl groups are preferred; aryloxycarbonyl groups such as phenyloxycarbonyl group, of which aryloxycarbonyl groups whose aryloxy moiety having 6 to 20 carbon atoms are preferred; and aralkyloxycarbonyl groups such as benzyloxycarbonyl group, of which aralkyloxy-carbonyl groups whose aralkyloxy moiety having 7 to 21 carbon atoms are preferred.

Exemplary acyl groups include aliphatic saturated or unsaturated acyl groups including aliphatic acyl groups having 1 to 30 carbon atoms, such as formyl, acetyl, propionyl, butyryl, isobutyryl, valeryl, pivaloyl, hexanoyl, decanoyl, and lauroyl groups, of which aliphatic acyl groups having 1 to 20 carbon atoms are preferred; acetoacetyl group; alicyclic acyl groups including cycloalkanecarbonyl groups such as cyclopentanecarbonyl and cyclohexanecarbonyl groups; and aromatic acyl groups such as benzoyl group.

Exemplary acyloxy groups include aliphatic saturated or unsaturated acyloxy groups including aliphatic acyloxy group having 1 to 30 carbon atoms, such as formyloxy, acetyloxy, propionyloxy, butyryloxy, isobutyryloxy, valeryloxy, pivaloyloxy, decanoyloxy, and lauroyloxy group, of which aliphatic acyloxy groups having 1 to 20 carbon atoms are preferred; acetoacetyloxy group; alicyclic acyloxy groups including cycloalkanecarbonyloxy groups such as cyclopentanecarbonyloxy and cyclohexanecarbonyloxy groups; and aromatic acyloxy groups such as benzoyloxy group.

The substituents $R^1$, $R^2$, $R^3$, $R^4$, $R^5$, and $R^6$ may be the same as or different from one another. At least two of $R^1$, $R^2$, $R^3$, $R^4$, $R^5$, and $R^6$ in Formula (2) may be bound to each other to form a double bond or an aromatic or nonaromatic ring together with a carbon atom or carbon-carbon bond constituting the cyclic imide skeleton. Preferred examples of the aromatic or nonaromatic ring are rings having about 5 to 12 members, of which rings having about 6 to 10 members are more preferred. The ring may be a heterocyclic or condensed heterocyclic ring (fused heterocyclic ring) but is often a hydrocarbon ring. Examples of such rings include alicyclic rings (e.g., substituted or unsubstituted cycloalkane rings such as cyclohexane ring; and substituted or unsubstituted cycloalkene rings such as cyclohexene ring), bridged rings (e.g., substituted or unsubstituted bridged hydrocarbon rings such as 5-norbornene ring), and substituted or unsubstituted aromatic rings (including fused rings (condensed rings)), such as benzene ring and naphthalene ring. The ring is often composed of an aromatic ring. The ring may have one or more substituents such as alkyl groups, haloalkyl groups, hydroxyl group, alkoxy groups, carboxyl group, substituted oxycarbonyl groups, acyl groups, acyloxy groups, nitro group, cyano group, amino group, and halogen atoms.

One or more cyclic imide groups represented by Formula (a) may further be formed on any of the substituents $R^1$, $R^2$, $R^3$, $R^4$, $R^5$, and $R^6$, or on the double bond or aromatic or nonaromatic ring formed by at least two of $R^1$, $R^2$, $R^3$, $R^4$, $R^5$, and $R^6$. For example, when $R^1$, $R^2$, $R^3$, $R^4$, $R^5$, or $R^6$ is an alkyl group having 2 or more carbon atoms, the cyclic imide group may be formed as including adjacent two carbon atoms constituting the alkyl group. When at least two of $R^1$, $R^2$, $R^3$, $R^4$, $R^5$, and $R^6$ are bound to each other to form a double bond together with a carbon-carbon bond constituting the cyclic imide skeleton, the cyclic imide group may be formed as including the double bond. When at least two of $R^1$, $R^2$, $R^3$, $R^4$, $R^5$, and $R^6$ are bound to each other to form an aromatic or nonaromatic ring together with a carbon atom or carbon-carbon bond constituting the cyclic imide skeleton, the cyclic imide group may be formed as including adjacent two carbon atoms constituting the ring.

Preferred cyclic imide compounds include compounds represented by the following formulae:

[Chemical Formula 4]

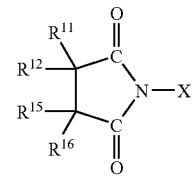

(3a)

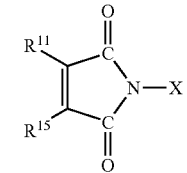

(3b)

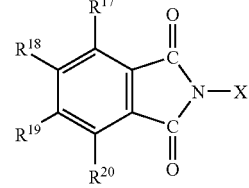

(3c)

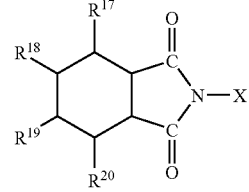

(3d)

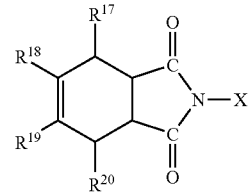

(3e)

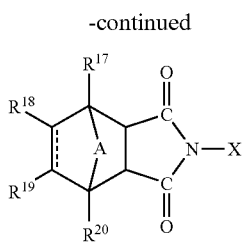
(3f)

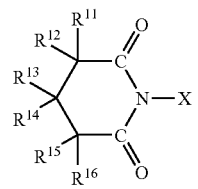
(3g)

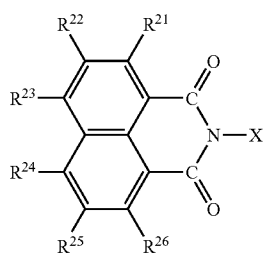
(3h)

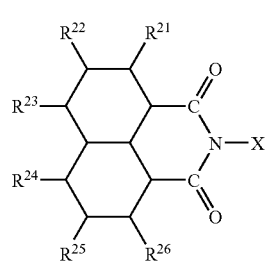
(3i)

wherein $R^{11}$, $R^{12}$, $R^{13}$, $R^{14}$, $R^{15}$, and $R^{16}$ are the same as or different from one another and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group; $R^{17}$, $R^{18}$, $R^{19}$, $R^{20}$, $R^{21}$, $R^{22}$, $R^{23}$, $R^{24}$, $R^{25}$, and $R^{26}$ are the same as or different from one another and each represent a hydrogen atom, an alkyl group, a haloalkyl group, a hydroxyl group, an alkoxy group, a carboxyl group, a substituted oxycarbonyl group, an acyl group, an acyloxy group, a nitro group, a cyano group, an amino group, or a halogen atom, or adjacent groups among $R^{17}$ to $R^{26}$ may be combined to form a 5- or 6-membered N-substituted cyclic imide skeleton shown in Formula (3c), (3d), (3e), (3f), (3h), or (3i); "A" in Formula (3f) represents a methylene group or an oxygen atom; and X is as defined above.

Examples of the halogen atoms, alkyl groups, aryl groups, cycloalkyl groups, hydroxyl group, alkoxy groups, carboxyl group, substituted oxycarbonyl groups, acyl groups, and acyloxy groups as the substituents $R^{11}$ to $R^{16}$ are as with the corresponding groups exemplified in the substituents $R^1$ to $R^6$.

In the substituents $R^{17}$ to $R^{26}$, exemplary alkyl groups include alkyl groups as with the above-exemplified alkyl groups, of which alkyl groups having about 1 to 6 carbon atoms are preferred; exemplary haloalkyl groups include haloalkyl groups having about 1 to 4 carbon atoms, such as trifluoromethyl group; exemplary alkoxy groups include alkoxy groups as above, of which lower alkoxy groups having about 1 to 4 carbon atoms are preferred; and exemplary substituted oxycarbonyl groups include substituted oxycarbonyl groups as above, such as alkoxycarbonyl groups, cycloalkyloxycarbonyl groups, aryloxycarbonyl groups, and aralkyloxycarbonyl groups. Exemplary acyl groups include acyl groups as above, such as aliphatic saturated or unsaturated acyl groups, acetoacetyl group, alicyclic acyl groups, and aromatic acyl groups; and exemplary acyloxy groups include acyloxy groups as above, such as aliphatic saturated or unsaturated acyloxy groups, acetoacetyloxy group, alicyclic acyloxy groups, and aromatic acyloxy groups. Exemplary halogen atoms include fluorine, chlorine, and bromine atoms. Each of the substituents $R^{17}$ to $R^{26}$ is often independently hydrogen atom, a lower alkyl group having about 1 to 4 carbon atoms, carboxyl group, a substituted oxycarbonyl group, nitro group, or a halogen atom.

Of the preferred imide compounds, representative examples of compounds having a 5-membered N-substituted cyclic imide skeleton include compounds of Formula (4) in which X is an —OR group and R is a hydrogen atom, such as N-hydroxysuccinimide, N-hydroxy-α-methylsuccinimide, N-hydroxy-α,α-dimethylsuccinimide, N-hydroxy-α,β-dimethylsuccinimide, N-hydroxy-α,α,β,β-tetramethylsuccinimide, N-hydroxymaleimide, N-hydroxyhexahydrophthalimide, N,N'-dihydroxycyclohexanetetracarboxylic diimide, N-hydroxyphthalimide, N-hydroxytetrabromophthalimide, N-hydroxytetrachlorophthalimide, N-hydroxy-HET acid imide (N-hydroxy-1,4,5,6,7,7-hexachloro-5-norbornene-2,3-dicarboximide), N-hydroxy-HIMIC acid imide (N-hydroxy-5-norbornene-2,3-dicarboximide), N-hydroxytrimellitimide, N,N'-dihydroxypyromellitic diimide, N,N'-dihydroxynaphthalenetetracarboxylic diimide, α,β-diacetoxy-N-hydroxysuccinimide, N-hydroxy-α,β-bis(propionyloxy)succinimide, N-hydroxy-α,β-bis(valeryloxy)succinimide, N-hydroxy-α,β-bis(lauroyloxy)succinimide, α,β-bis(benzoyloxy)-N-hydroxysuccinimide, N-hydroxy-4-methoxycarbonylphthalimide, 4-chloro-N-hydroxyphthalimide, 4-ethoxycarbonyl-N-hydroxyphthalimide, N-hydroxy-4-pentyloxycarbonylphthalimide, 4-dodecyloxy-N-hydroxycarbonylphthalimide, N-hydroxy-4-phenoxycarbonylphthalimide, N-hydroxy-4,5-bis(methoxycarbonyl)phthalimide, 4,5-bis(ethoxycarbonyl)-N-hydroxyphthalimide, N-hydroxy-4,5-bis(pentyloxycarbonyl)phthalimide, 4,5-bis(dodecyloxycarbonyl)-N-hydroxyphthalimide, and N-hydroxy-4,5-bis(phenoxycarbonyl)phthalimide; compounds corresponding to these compounds, except that R is an acyl group such as acetyl group, propionyl group, or benzoyl group; compounds of Formula (4) in which X is an —OR group and R is a group capable of forming an acetal or hemiacetal bond with hydroxyl group(s), such as N-methoxymethyloxyphthalimide, N-(2-methoxyethoxymethyloxy) phthalimide, and N-tetrahydropyranyloxyphthalimide; compounds of Formula (4) in which X is an —OR group and R is a sulfonyl group, such as N-methanesulfonyloxyphthalimide and N-(p-toluenesulfonyloxy)phthalimide; and compounds of Formula (4) in which X is an —OR group and R is a group corresponding to an inorganic acid, except for removing hydroxyl group (OH group) therefrom, such as sulfuric acid ester, nitric acid ester, phosphoric ester, or boric acid ester of N-hydroxyphthalimide.

Of the preferred imide compounds, representative examples of compounds having a 6-membered N-substituted cyclic imide skeleton include compounds of Formula (4) in which X is an —OR group and R is a hydrogen atom, such as N-hydroxyglutarimide, N-hydroxy-α,α-dimethylglutarimide, N-hydroxy-β,β-dimethylglutarimide, N-hydroxy-1,8-decahydronaphthalenedicarboximide, N,N'-dihydroxy-1,8;4,5-decahydronaphthalenetetracarboxylic diimide, N-hydroxy-1,8-naphthalenedicarboximide (N-hydroxynaphthalimide), and N,N'-dihydroxy-1,8;4,5-naphthalenetetracarboxylic diimide; compounds corresponding to these compounds, except that R is an acyl group such as acetyl group, propionyl group, or benzoyl group; compounds of Formula (4) in which X is an —OR group and R is a group capable of forming an acetal or hemiacetal bond with hydroxyl group(s), such as N-methoxymethyloxy-1,8-naphthalenedicarboximide and N,N'-bis(methoxymethyloxy)-1, 8;4,5-naphthalenetetracarboxylic diimide; compounds of Formula (4) in which X is an —OR group and R is a sulfonyl group, such as N-methanesulfonyloxy-1,8-naphthalenedicarboximide and N,N'-bis(methanesulfonyloxy)-1,8;4,5-naphthalenetetracarboxylic diimide; and compounds of Formula (4) in which X is an —OR group and R is a group corresponding to an inorganic acid, except for removing hydroxyl group (OH group) therefrom, such as a sulfuric acid ester, nitric acid ester, phosphoric ester, or boric acid ester of N-hydroxy-1,8-naphthalenedicarboximide or N,N'-dihydroxy-1,8;4,5-naphthalenetetracarboxylic diimide.

Examples of the nitrogen-containing cyclic compounds containing the skeleton represented by Formula (1) as a ring constituent further include, in addition to the cyclic imide compounds, cyclic acylurea compounds having a cyclic acylurea skeleton [—C(=O)—N—C(=O)—N—]. Representative examples of the cyclic acylurea compounds include hydro-1-hydroxy (or 1-(substituted oxy))-1,3,5-triazine-2,6-dione compounds represented by following Formula (4):

[Chemical Formula 5]

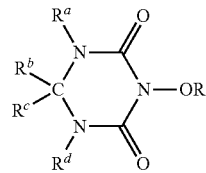

(4)

wherein $R^a$ and $R^d$ are the same as or different from one another and each represent a hydrogen atom, an alkyl group, an aryl group, a cycloalkyl group, a protected or unprotected hydroxyl group, a protected or unprotected carboxyl group, or an acyl group; $R^b$ and $R^c$ are the same as or different from each other and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group, in which at least two of $R^a$, $R^b$, $R^c$, and $R^d$ may be bound to each other to form a double bond or an aromatic or nonaromatic ring together with an atom constituting the ring in the formula, and wherein $R^b$ and $R^c$ may together form an oxo group; and R is as defined above.

In Formula (4), examples of the alkyl groups, aryl groups, cycloalkyl groups, and acyl groups as $R^a$ and $R^d$ are as with the alkyl groups and other groups exemplified as the substituents $R^1$ to $R^6$. Exemplary protecting groups for hydroxyl group (hydroxyl-protecting groups) are as mentioned above.

Exemplary protecting groups for carboxyl group (carboxyl-protecting groups) include protecting groups commonly used in organic synthesis, including alkoxy groups (e.g., alkoxy groups having 1 to 6 carbon atoms, such as methoxy, ethoxy, and butoxy), cycloalkyloxy groups, aryloxy groups (e.g., phenoxy group), aralkyloxy groups (e.g., benzyloxy group), trialkylsilyloxy groups (e.g., trimethylsilyloxy group), substituted or unsubstituted amino groups (e.g., amino group; and mono- or di-(alkyl)amino groups whose alkyl moiety having 1 to 6 carbon atoms, such as methylamino group and dimethylamino group).

Examples of the halogen atoms, alkyl groups, aryl groups, cycloalkyl groups, hydroxyl group, alkoxy groups, carboxyl group, substituted oxycarbonyl groups, acyl groups, and acyloxy groups as $R^b$ and $R^c$ are as with the alkyl groups and other groups exemplified as the substituents $R^1$ to $R^6$.

In Formula (4), at least two of $R^a$, $R^b$, $R^c$, and $R^d$ may be bound to each other to form a double bond, or an aromatic or nonaromatic ring together with an atom (carbon atom and/or nitrogen atom) constituting the ring in the formula, and/or $R^b$ and $R^c$ may together form an oxo group. Preferred examples of the aromatic or nonaromatic ring are as above.

Of the compounds represented by Formula (4), preferred are isocyanuric acid derivatives represented by following Formula (4a):

[Chemical Formula 6]

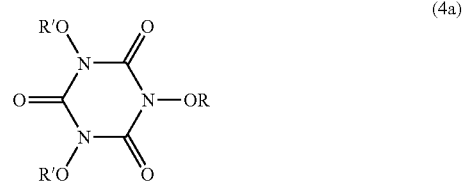

(4a)

wherein R, R', and R" are the same as or different from one another and each represent a hydrogen atom or a hydroxyl-protecting group.

Representative examples of compounds belonging to the cyclic acylurea compounds include hexahydro-1,3,5-trihydroxy-1,3,5-triazine-2,4,6-trione (i.e., 1,3,5-trihydroxyisocyanuric acid), 1,3,5-triacetoxy-hexahydro-1,3,5-triazine-2,4,6-trione, hexahydro-1,3,5-tris(methoxymethyloxy)-1,3,5-triazine-2,4,6-trione, hexahydro-1-hydroxy-1,3,5-triazine-2,6-dione, hexahydro-1-hydroxy-3,5-dimethyl-1,3,5-triazine-2,6-dione, 1-acetoxy-hexahydro-1,3,5-triazine-2,6-dione, and 1-acetoxy-hexahydro-3,5-dimethyl-1,3,5-triazine-2,6-dione.

Of the nitrogen-containing cyclic compounds, compounds in which X is an —OR group and R is a hydrogen atom (N-hydroxy cyclic compounds) can be prepared according to a known process or a combination of known processes. Of the nitrogen-containing cyclic compounds, compounds in which X is an —OR group and R is a hydroxyl-protecting group can be prepared by introducing a desired protecting group into corresponding compounds in which R is a hydrogen atom (N-hydroxy cyclic compounds) using a common reaction for introducing such protecting groups.

Specifically, of the cyclic imide compounds, compounds in which X is an —OR group and R is a hydrogen atom (N-hydroxy cyclic imide compounds) can be prepared by a common imidization process (a process for the formation of an imide), such as a process that includes the steps of reacting a corresponding acid anhydride with hydroxylamine for ring-opening of the acid anhydride group, and closing the ring to form an imide. For example, N-acetoxyphthalimide can be prepared by reacting N-hydroxyphthalimide with acetic anhydride or by reacting N-hydroxyphthalimide with an acetyl halide in the presence of a base. The compounds can also be prepared by other processes.

Of the cyclic acylurea compounds, for example, 1,3,5-triacetoxy-hexahydro-1,3,5-triazine-2,4,6-trione (i.e., 1,3,5-triacetoxyisocyanuric acid) can be prepared by reacting hexahydro-1,3,5-trihydroxy-1,3,5-triazine-2,4,6-trione (i.e., 1,3,5-trihydroxyisocyanuric acid) with acetic anhydride, or by reacting hexahydro-1,3,5-trihydroxy-1,3,5-triazine-2,4,6-trione with an acetyl halide in the presence of a base.

Examples of cyclic imide compounds especially preferred as catalysts include N-hydroxy cyclic imide compounds (e.g., N-hydroxysuccinimide, N-hydroxyphthalimide, N,N'-dihydroxypyromellitic diimide, N-hydroxyglutarimide, N-hydroxy-1,8-naphthalenedicarboximide, and N,N'-dihydroxy-1,8:4,5-naphthalenetetracarboxylic diimide) derived from aliphatic polycarboxylic acid anhydrides (cyclic anhydrides) or derived from aromatic polycarboxylic acid anhydrides (cyclic anhydrides); compounds corresponding to these N-hydroxy cyclic imide compounds, except for introducing a protecting group into hydroxyl group thereof; and cyclic acylurea compounds.

Each of different nitrogen-containing cyclic compounds containing the skeleton represented by Formula (1) as a ring constituent can be used alone or in combination. The nitrogen-containing cyclic compounds may be formed within the reaction system. The nitrogen-containing cyclic compounds may be used as being supported by a support (carrier). The support used herein is often a porous support such as activated carbon, zeolite, silica, silica-alumina, or bentonite. The amount of the nitrogen-containing cyclic compounds on the support is, for example, about 0.1 to 50 parts by weight, preferably about 0.5 to 30 parts by weight, and more preferably about 1 to 20 parts by weight, per 100 parts by weight of the support.

The reaction system herein may contain a free-radical generator (e.g., a free-radical initiator) and/or a free-radical reaction accelerator. Examples of such components include halogens such as chlorine and bromine; peracids such as peracetic acid and m-chloroperbenzoic acid; peroxides including hydroperoxides, such as hydrogen peroxide and t-butyl hydroperoxide (TBHP); azo compounds such as azobisisobutyronitrile; acetophenones; cyclic amine-N-oxyl compounds; nitric acid or nitrous acid, or salts of them; nitrogen dioxide; and aldehydes such as benzaldehyde (e.g., when the target compound is an aromatic carboxylic acid or aromatic carboxylic anhydride, an aldehyde corresponding to the target compound (oxidized product)). The presence of these components in the system may accelerate the reaction. The amount of the components is typically about 0.0001 to 1.0 mole and preferably about 0.001 to 0.7 mole, per 1 mole of the nitrogen-containing cyclic compounds containing the skeleton represented by Formula (1) as a ring constituent.

Process for Oxidation of Organic Compounds

A process for the oxidation of an organic compound (i.e., process for the production of an oxygen-containing organic compound), according to the present invention, includes oxidizing an organic compound with molecular oxygen in a liquid phase in the presence of the catalysts to give an oxygen-containing organic compound.

The organic compound used as a reaction material (substrate) is not especially limited, as long as being a compound that is oxidizable with oxygen in the presence of the catalysts. The substrate is preferably a compound (A) capable of forming a stable free radical. Representative examples of such compounds include (A1) heteroatom-containing compounds having a carbon-hydrogen bond at an adjacent position to the heteroatom; (A2) compounds having a carbon-heteroatom double bond; (A3) compounds having a methine carbon atom; (A4) compounds having a carbon-hydrogen bond at an adjacent position to an unsaturated bond; (A5) nonaromatic cyclic hydrocarbons; (A6) conjugated compounds; (A7) aromatic compounds; (A8) linear alkanes; and (A9) olefins.

Each of these compounds may have one or more substituents within ranges not adversely affecting the reaction. Exemplary substituents include halogen atoms, hydroxyl group, mercapto group, oxo group, substituted oxy groups (e.g., alkoxy groups, aryloxy groups, and acyloxy groups), substituted thio groups, carboxyl group, substituted oxycarbonyl groups, substituted or unsubstituted carbamoyl groups, cyano group, nitro group, substituted or unsubstituted amino groups, sulfo group, alkyl groups, alkenyl groups, alkynyl groups, alicyclic hydrocarbon groups, aromatic hydrocarbon groups, and heterocyclic groups.

Exemplary heteroatom-containing compounds (A1) having a carbon-hydrogen bond at an adjacent position to the heteroatom include (A1-1) primary or secondary alcohols and primary or secondary thiols; (A1-2) ethers having a carbon-hydrogen bond at an adjacent position to oxygen atom, and sulfides having a carbon-hydrogen bond at an adjacent position to the sulfur atom; and (A1-3) acetals (including hemiacetals) having a carbon-hydrogen bond at an adjacent position to oxygen atom, and thioacetals (including thiohemiacetals) having a carbon-hydrogen bond at an adjacent position to the sulfur atom.

The primary or secondary alcohols as the compounds (A1-1) include a wide variety of alcohols. These alcohols may be whichever of monohydric, dihydric, and polyhydric alcohols.

Representative examples of primary alcohols include saturated or unsaturated aliphatic primary alcohols having about 1 to 30 carbon atoms, such as methanol, ethanol, 1-propanol, 1-butanol, 1-pentanol, 1-hexanol, 1-octanol, 1-decanol, 2-buten-1-ol, ethylene glycol, trimethylene glycol, hexamethylene glycol, and pentaerythritol, of which those having about 1 to 20 carbon atoms are preferred, and those having about 1 to 15 carbon atoms are more preferred; saturated or unsaturated alicyclic primary alcohols such as cyclopentylmethyl alcohol, cyclohexylmethyl alcohol, and 2-cyclohexylethyl alcohol; aromatic primary alcohols such as benzyl alcohol, 2-phenylethyl alcohol, 3-phenylpropyl alcohol, and cinnamic alcohol; and heterocyclic alcohols such as 2-hydroxymethylpyridine.

Representative examples of secondary alcohols include saturated or unsaturated aliphatic secondary alcohols having about 3 to 30 carbon atoms, such as 2-propanol, s-butyl alcohol, 2-pentanol, 2-octanol, 2-penten-4-ol, as well as vicinal diols such as 1,2-propanediol, 2,3-butanediol, and 2,3-pentanediol, of which those having about 3 to 20 carbon atoms are preferred, and those having about 3 to 15 carbon atoms are more preferred; secondary alcohols having an aliphatic hydrocarbon group and an alicyclic hydrocarbon group (e.g., a cycloalkyl group) bound to a hydroxyl-binding carbon atom, such as 1-cyclopentylethanol and 1-cyclohexylethanol; saturated or unsaturated alicyclic secondary alcohols (including bridged secondary alcohols) having about 3 to 20 members, such as cyclopentanol, cyclohexanol, cyclooctanol, cyclododecanol, 2-cyclohexen-1-ol, 2-adamantanol, 2-adamantanols each having one to four hydroxyl groups at the bridgehead positions, and 2-adamantanols having oxo group on the adamantane ring, of which those having about 3 to 15 members are preferred, those having about 5 to 15 members are more preferred, and those having about 5 to 8 members are especially preferred; aromatic secondary alcohols such as 1-phenylethanol; and heterocyclic secondary alcohols such as 1-(2-pyridyl)ethanol.

Representative examples of alcohols further include alcohols having a bridged hydrocarbon group (e.g., compounds having a bridged hydrocarbon group bound to a hydroxyl-binding carbon atom), such as 1-adamantanemethanol, α-methyl-1-adamantanemethanol, 3-hydroxy-α-methyl-1-adamantanemethanol, 3-carboxy-α-methyl-1-adamantanemethanol, α-methyl-3a-perhydroindenemethanol, α-methyl-4-α-decahydronaphthalenemethanol, α-methyl-4-α-perhydrofluorenemethanol, α-methyl-2-tricyclo[5.2.1.0$^{2,6}$]decanemethanol, and α-methyl-1-norbornanemethanol.

Preferred alcohols include the secondary alcohols and the alcohols having a bridged hydrocarbon group. Exemplary preferred secondary alcohols include aliphatic secondary alcohols such as 2-propanol and s-butyl alcohol; secondary alcohols having an aliphatic hydrocarbon group (e.g., an alkyl group having 1 to 4 carbon atoms or an aryl group having 6 to 14 carbon atoms) and a nonaromatic carbocyclic group (e.g., a cycloalkyl or cycloalkenyl group having 3 to 15 carbon atoms) bound to a hydroxyl-binding carbon atom, such as 1-cyclohexylethanol; alicyclic secondary alcohols having about 3 to 15 members, such as cyclopentanol, cyclohexanol, and 2-adamantanol; and aromatic secondary alcohols such as 1-phenylethanol.

Exemplary primary or secondary thiols as the compounds (A1-1) include thiols corresponding to the above-mentioned primary or secondary alcohols.

Exemplary ethers having a carbon-hydrogen bond at an adjacent position to oxygen atom, as the compounds (A1-2), include aliphatic ethers such as dimethyl ether, diethyl ether, dipropyl ether, diisopropyl ether, dibutyl ether, and diallyl ether; aromatic ethers such as anisole, phenetole, dibenzyl ether, and phenyl benzyl ether; and cyclic ethers (to which an aromatic ring or nonaromatic ring may be condensed), such as dihydrofuran, tetrahydrofuran, pyran, dihydropyran, tetrahydropyran, morpholine, chroman, and isochroman.

Exemplary sulfides having a carbon-hydrogen bond at an adjacent position to the sulfur atom, as the compounds (A1-2), include sulfides corresponding to the above-mentioned ethers having a carbon-hydrogen bond at an adjacent position to oxygen atom.

Exemplary acetals having a carbon-hydrogen bond at an adjacent position to oxygen atom, as the compounds (A1-3), include acetals each derived from an aldehyde and an alcohol or acid anhydride. The acetals include cyclic acetals and acyclic acetals. Examples of the aldehyde include aliphatic aldehydes such as formaldehyde, acetaldehyde, propionaldehyde, butylaldehyde, and isobutylaldehyde; alicyclic aldehydes such as cyclopentanecarbaldehyde and cyclohexanecarbaldehyde; and aromatic aldehydes such as benzaldehyde and phenylacetaldehyde. Examples of the alcohol include monohydric alcohols such as methanol, ethanol, 1-propanol, 1-butanol, and benzyl alcohol; and dihydric alcohols such as ethylene glycol, propylene glycol, 1,3-propanediol, and 2,2-dibromo-1,3-propanediol. Representative examples of the acetals include 1,3-dioxolane compounds such as 1,3-dioxolane, 2-methyl-1,3-dioxolane, and 2-ethyl-1,3-dioxolane; 1,3-dioxane compounds such as 2-methyl-1,3-dioxane; and dialkyl acetal compounds such as acetaldehyde dimethyl acetal.

Exemplary thioacetals having a carbon-hydrogen bond at an adjacent position to the sulfur atom, as the compounds (A1-3), include thioacetals corresponding to the above-mentioned acetals having a carbon-hydrogen bond at an adjacent position to oxygen atom.

Examples of the compounds (A2) having a carbon-heteroatom double bond include (A2-1) carbonyl-containing compounds; (A2-2) thiocarbonyl-containing compounds; and (A2-3) imines. The carbonyl-containing compounds (A2-1) include ketones and aldehydes. Exemplary ketones and aldehydes include chain ketones such as acetone, methyl ethyl ketone, methyl isobutyl ketone, 3-pentanone, methyl vinyl ketone, methyl cyclohexyl ketone, and acetophenone; cyclic ketones such as cyclopentanone, cyclohexanone, 4-methylcyclohexanone, isophorone, cyclodecanone, cyclododecanone, 1,4-cyclooctanedione, 2,2-bis(4-oxocyclohexyl)propane, and 2-adamantanone; 1,2-dicarbonyl compounds (e.g., α-diketones), such as biacetyl (2,3-butanedione), bibenzoyl (benzil), acetylbenzoyl, and cyclohexane-1,2-dione; α-keto-alcohols such as acetoin and benzoin; aliphatic aldehydes such as acetaldehyde, propionaldehyde, butanal, hexanal, succinaldehyde, glutaraldehyde, and adipaldehyde; alicyclic aldehydes such as cyclohexyl aldehyde, citral, and citronellal; aromatic aldehydes such as benzaldehyde, carboxybenzaldehyde, nitrobenzaldehyde, cinnamaldehyde, salicylaldehyde, anisaldehyde, phthalaldehyde, isophthalaldehyde, and terephthalaldehyde; and heterocyclic aldehydes such as furfural and nicotinaldehyde.

Exemplary thiocarbonyl-containing compounds (A2-2) include thiocarbonyl-containing compounds corresponding to the above-mentioned carbonyl-containing compounds (A2-1).

Exemplary imines (A2-3) include imines (also including oximes and hydrazones) derived from any of the carbonyl-containing compounds (A2-1) and ammonia or an amine. Exemplary amines include amines such as methylamine, ethylamine, propylamine, butylamine, hexylamine, benzylamine, cyclohexylamine, and aniline; hydroxylamines such as hydroxylamine and O-methylhydroxylamine; and hydrazines such as hydrazine, methylhydrazine, and phenylhydrazine.

The compounds (A3) having a methine carbon atom include (A3-1) cyclic compounds having a methine group (i.e., a methine carbon-hydrogen bond) as a ring-constituting unit; and (A3-2) chain compounds having a methine carbon atom.

Exemplary cyclic compounds (A3-1) include (A3-1a) bridged cyclic compounds having at least one methine group; and (A3-1b) nonaromatic cyclic compounds (e.g., alicyclic hydrocarbons) having a hydrocarbon group bound to the ring. The bridged cyclic compounds further include compounds in which two rings have two carbon atoms in common, such as hydrogenated products of condensed polycyclic aromatic hydrocarbons.

Exemplary bridged compounds (A3-1a) include bridged cyclic hydrocarbons or bridged heterocyclic compounds each having two to four rings, such as decahydronaphthalene, bicyclo[2.2.0]hexane, bicyclo[2.2.2]octane, bicyclo[3.2.1]octane, bicyclo[4.3.2]undecane, bicyclo[3.3.3]undecane, thujone, carane, pinane, pinene, bornane, bornylene, norbornane, norbornene, camphor, camphoric acid, camphene, tricyclene, tricyclo[5.2.1.0$^{3,8}$]decane, tricyclo[4.2.1.1$^{2,5}$]decane, exotricyclo[5.2.1.0$^{2,6}$]decane, endotricyclo[5.2.1.0$^{2,6}$]decane, tricyclo[4.3.1.1$^{2,5}$]undecane, tricyclo[4.2.2.1$^{2,5}$]undecane, endotricyclo[5.2.2.0$^{2,6}$]undecane, adamantane, 1-adamantanol, 1-chloroadamantane, 1-methyladamantane, 1,3-dimethyladamantane, 1-methoxyadamantane, 1-carboxyadamantane, 1-methoxycarbonyladamantane, 1-nitroadamantane, tetracyclo[4.4.0.1$^{2,5}$.1$^{7,10}$]dodecane, perhydroanthracene, perhydroacenaphthene, perhydrophenanthrene, perhydrophenalene, perhydroindene, and quinuclidine; and derivatives of them. These bridged compounds have a methine carbon atom at a bridgehead position (corresponding to a junction site when two rings have two atoms in common).

Exemplary nonaromatic cyclic compounds (A3-1b) having a hydrocarbon group bound to the ring include alicyclic hydrocarbons having about 3 to 15 members and containing a hydrocarbon group (e.g., an alkyl group) bound to the ring, and derivatives thereof, such as 1-methylcyclopentane, 1-methylcyclohexane, limonene, menthene, menthol, carvomenthone, and menthone. The hydrocarbon group just mentioned above may have about 1 to 20 carbon atoms, and preferably about 1 to 10 carbon atoms. The nonaromatic cyclic compounds (A3-1b) having a hydrocarbon group bound to the ring have a methine carbon atom at the bonding site between the ring and the hydrocarbon group.

Exemplary chain compounds (A3-2) having a methine carbon atom include chain hydrocarbons having a tertiary carbon atom, including aliphatic hydrocarbons having about 4 to 20 (preferably about 4 to 10) carbon atoms, such as isobutane, isopentane, isohexane, 3-methylpentane, 2,3-dimethylbutane, 2-methylhexane, 3-methylhexane, 3,4-dimethylhexane, and 3-methyloctane; and derivatives of them.

Examples of the compounds (A4) having a carbon-hydrogen bond at an adjacent position to an unsaturated bond include (A4-1) aromatic compounds having a methyl group or methylene group at an adjacent position to the aromatic ring (at a "benzylic position"); and (A4-2) nonaromatic compounds having a methyl group or methylene group at an adjacent position to an unsaturated bond (e.g., carbon-carbon unsaturated bond or carbon-oxygen double bond).

The aromatic rings in the aromatic compounds (A4-1) may each be whichever of an aromatic hydrocarbon ring and an aromatic heterocyclic ring (heteroaromatic ring). Exemplary aromatic hydrocarbon rings include benzene ring and condensed carbon rings. Exemplary condensed carbon rings include condensed carbon rings each having condensed two to ten carbon rings each having 4 to 7 members, such as naphthalene, azulene, indacene, anthracene, phenanthrene, triphenylene, and pyrene. Exemplary aromatic heterocyclic rings include heterocyclic rings containing oxygen atom as a heteroatom, including 5-membered rings (e.g., furan, oxazole, and isoxazole), 6-membered rings (e.g., 4-oxo-4H-pyran), and condensed rings (e.g., benzofuran, isobenzofuran, and 4-oxo-4H-chromene); heterocyclic rings containing sulfur atom as a heteroatom, including 5-membered rings (e.g., thiophene, thiazole, isothiazole, and thiadiazole), 6-membered rings (e.g., 4-oxo-4H-thiopyran), and condensed rings (e.g., benzothiophene); and heterocyclic rings containing nitrogen atom as a heteroatom, including 5-membered rings (e.g., pyrrole, pyrazole, imidazole, and triazole), 6-membered rings (e.g., pyridine, pyridazine, pyrimidine, and pyrazine), and condensed rings (e.g., indole, quinoline, acridine, naphthyridine, quinazoline, and purine).

The methylene group at an adjacent position to the aromatic ring may be a methylene group constituting a nonaromatic ring condensed to the aromatic ring. The compounds (A4-1) may each have both methyl group and methylene group at an adjacent position to the aromatic ring.

Exemplary aromatic compounds having a methyl group at an adjacent position to the aromatic ring include aromatic hydrocarbons whose aromatic ring having about one to six methyl groups substituted thereon, such as toluene, o-xylene, m-xylene, p-xylene, o-t-butyltoluene, m-t-butyltoluene, p-t-butyltoluene, 1-ethyl-4-methylbenzene, 1-ethyl-3-methylbenzene, 1-isopropyl-4-methylbenzene, 1-t-butyl-4-methylbenzene, 1-methoxy-4-methylbenzene, mesitylene, pseudocumene, durene, methylnaphthalene, dimethylnaphthalene, methylanthracene, 4,4'-dimethylbiphenyl, tolualdehyde, dimethylbenzaldehyde, trimethylbenzaldehyde, toluic acid, trimethylbenzoic acid, and dimethylbenzoic acid; and heterocyclic compounds whose heterocycle having about one to six methyl groups substituted thereon, such as 2-methylfuran, 3-methylfuran, 3-methylthiophene, 2-methylpyridine, 3-methylpyridine, 4-methylpyridine, 2,4-dimethylpyridine, 2,4,6-trimethylpyridine, 4-methylindole, 2-methylquinoline, and 3-methylquinoline.

Exemplary aromatic compounds having a methylene group at an adjacent position to the aromatic ring include aromatic hydrocarbons each containing an alkyl group or substituted alkyl group having 2 or more carbon atoms, such as ethylbenzene, propylbenzene, butylbenzene, 1,4-diethylbenzene, and diphenylmethane; aromatic heterocyclic compounds containing an alkyl group or substituted alkyl group having 2 or more carbon atoms, such as 2-ethylfuran, 3-propylthiophene, 4-ethylpyridine, and 4-butylquinoline; and compounds having a nonaromatic ring condensed to the aromatic ring, which nonaromatic ring having methylene group at an adjacent position to the aromatic ring, such as dihydronaphthalene, indene, indane, tetrahydronaphthalene (tetralin), fluorene, acenaphthene, phenalene, indanone, and xanthene.

The nonaromatic compounds (A4-2) having a methyl group or methylene group at an adjacent position to an unsaturated bond include (A4-2a) chain unsaturated hydrocarbons having a methyl group or methylene group at an "allylic position"; and (A4-2b) compounds having a methyl group or methylene group at an adjacent position to a carbonyl group.

Examples of the chain unsaturated hydrocarbons (A4-2a) include chain unsaturated hydrocarbons having about 3 to 20 carbon atoms, such as propylene, 1-butene, 2-butene, 1-pentene, 1-hexene, 2-hexene, 1,5-hexadiene, 1-octene, 3-octene, and undecatriene. Exemplary compounds (A4-2b) include ketones (e.g., chain ketones such as acetone, methyl ethyl ketone, 3-pentanone, and acetophenone; and cyclic ketones such as cyclohexanone) and carboxylic acids and derivatives thereof (e.g., acetic acid, propionic acid, butanoic acid, pentanoic acid, hexanoic acid, heptanoic acid, phenylacetic acid, malonic acid, succinic acid, glutaric acid, and esters of them).

The nonaromatic cyclic hydrocarbons (A5) include (A5-1) cycloalkanes; and (A5-2) cycloalkenes.

Exemplary cycloalkanes (A5-1) include compounds having a cycloalkane ring containing 3 to 30 members, such as cyclopropane, cyclobutane, cyclopentane, cyclohexane, cycloheptane, cyclooctane, cyclononane, cyclodecane, cyclododecane, cyclotetradecane, cyclohexadecane, cyclotetracosane, and cyclotriacontane; and derivatives of them. Preferred cycloalkane rings include cycloalkane rings containing 5 to 30 members, of which cycloalkane rings containing 5 to 20 members are more preferred.

Exemplary cycloalkenes (A5-2) include compounds having a cycloalkene ring containing 3 to 30 members, such as cyclopropene, cyclobutene, cyclopentene, cyclooctene, cyclohexene, 1-methyl-cyclohexene, isophorone, cycloheptene, and cyclododecene; cycloalkadienes such as cyclopentadiene, 1,3-cyclohexadiene, and 1,5-cyclooctadiene; cycloalkatrienes such as cyclooctatriene; and derivatives of them. Preferred cycloalkenes include compounds having a ring containing 3 to 20 members, of which compounds having a ring containing 3 to 12 members are more preferred.

The conjugated compounds (A6) include (A6-1) conjugated dienes; (A6-2) α,β-unsaturated nitriles; and (A6-3) α,β-unsaturated carboxylic acids and derivatives thereof (e.g., esters, amides, and acid anhydrides).

Exemplary conjugated dienes (A6-1) include butadiene, isoprene, 2-chlorobutadiene, and 2-ethylbutadiene. As used herein the "conjugated dienes (A6-1)" further include compounds having both a double bond and a triple bond conjugated with each other, such as vinylacetylene.

Exemplary α,β-unsaturated nitriles (A6-2) include (meth)acrylonitriles. Exemplary α,β-unsaturated carboxylic acids and derivatives thereof (A6-3) include (meth)acrylic acids; (meth)acrylic esters such as methyl (meth)acrylates, ethyl (meth)acrylates, isopropyl (meth)acrylates, butyl (meth)acrylates, and 2-hydroxyethyl (meth)acrylates; and (meth)acrylamides and (meth)acrylamide derivatives such as N-methylol(meth)acrylamides.

Examples of the aromatic hydrocarbons (A7) include aromatic compounds having at least one benzene ring, such as benzene, naphthalene, acenaphthylene, phenanthrene, anthracene, and naphthacene, of which condensed polycyclic aromatic compounds each having at least two or more (e.g., two to ten) benzene rings being condensed are preferred. These aromatic hydrocarbons may each have one or more substituents. Specific examples of such aromatic hydrocarbons having one or more substituents include 2-chloronaphthalene, 2-methoxynaphthalene, 1-methylnaphthalene, 2-methylnaphthalene, 1-bromoanthracene, 2-methylanthracene, 2-t-butylanthracene, 2-carboxyanthracene, 2-ethoxycarbonylanthracene, 2-cyanoanthracene, 2-nitroanthracene, and 2-methylpentalene. To the benzene ring(s), a nonaromatic carbon ring, aromatic heterocyclic ring, or nonaromatic heterocyclic ring may be condensed.

Examples of the linear alkanes (A8) include linear alkanes having about 1 to 30 carbon atoms, such as methane, ethane, propane, butane, pentane, hexane, heptane, octane, nonane, decane, dodecane, tetradecane, and hexadecane, of which those having about 1 to 20 carbon atoms are preferred.

The olefins (A9) may be whichever of α-olefins and internal olefins, each of which may have one or more substituents (e.g., the aforementioned substituents such as hydroxyl group and acyloxy groups). The olefins (A9) also include dienes and other olefins each having two or more carbon-carbon double bonds. Examples of the olefins (A9) include chain olefins such as ethylene, propylene, 1-butene, 2-butene, isobutene, 1-hexene, 2-hexene, 1-acetoxy-3,7-dimethyl-2,6-octadiene, styrene, vinyltoluene, α-methylstyrene, 3-vinylpyridine, and 3-vinylthiophene; and cyclic olefins such as cyclopentene, cyclohexene, cycloheptene, cyclooctene, cyclodecene, cyclododecene, 1,4-cyclohexadiene, limonene, 1-p-menthene, 3-p-menthene, carveol, bicyclo[2.2.1]hept-2-ene, bicyclo[3.2.1]oct-2-ene, α-pinene, and 2-bornene.

Each of different compounds (A) capable of forming a free radical may be used alone or in combination, and in the latter case, the compounds used in combination may belong to the same or different categories. When two or more of these compounds, especially two or more of these compounds belonging to different categories, are used in the reaction, one of the substrates may act as a co-reacting agent (e.g., co-oxidizing agent) with respect to the other, and this may significantly improve the reaction rate.

Among the substrates, especially preferred substrates for use in the present invention are hydrocarbons including hydrocarbons each having a methine carbon atom, such as adamantane and other bridged compounds having a methine group; aromatic hydrocarbons having a methyl group or methylene group at an adjacent position to the aromatic ring, such as toluene and xylenes; and nonaromatic cyclic hydrocarbons such as cyclohexane and other cycloalkanes. The present invention can industrially efficiently produce, for example, hydroperoxides, alcohols, carbonyl compounds, and/or carboxylic acids in high yields from such hydrocarbons.

Molecular oxygen can be used as an oxidizing agent. The oxygen may be formed within the reaction system. The molecular oxygen is not especially limited and can be whichever of pure oxygen; a diluted oxygen diluted with an inert gas such as nitrogen, helium, argon, or carbon dioxide gas; and air at normal atmospheric pressure or under a pressure (1 to 100 atmospheres). Though suitably selectable according to the type(s) of the substrate(s), the amount of the molecular oxygen is generally about 0.5 mole or more (e.g., 1 mole or more), preferably about 1 to 100 moles, and more preferably about 2 to 50 moles, per 1 mole of the substrate(s). The molecular oxygen is often used in excess moles to the substrate(s).

The amount of the transition metal compound(s) supported on the solid superacid is, in terms of metal atoms in the transition metal compound(s), about 0.0001 to 50 percent by mole and especially preferably about 0.0001 to 5 percent by mole, relative to the amount of the substrate(s).

The amount of the nitrogen-containing cyclic compound(s) is about 0.0001 to 50 percent by mole and especially preferably about 0.01 to 20 percent by mole, relative to the amount of the substrate(s).

The oxidation reaction in the present invention is performed in a liquid phase in the presence of, or in the absence of, a solvent. When the oxidation reaction is performed in the presence of a solvent, exemplary solvents include organic acids such as acetic acid and propionic acid; nitriles such as acetonitrile, propionitrile, and benzonitrile; amides such as formamide, acetamide, dimethylformamide (DMF), and dimethylacetamide; aliphatic hydrocarbons such as hexane and octane; halogenated hydrocarbons such as chloroform, dichloromethane, dichloroethane, carbon tetrachloride, chlorobenzene, and trifluoromethylbenzene; nitro compounds such as nitrobenzene, nitromethane, and nitroethane; esters such as ethyl acetate and butyl acetate; and mixtures of these solvents. Among them, acetic acid and ethyl acetate are preferred as the solvent, of which acetic acid is more preferred. The amount of the solvent is preferably chosen so that the concentration of the substrate be typically about 0.01 to 80 percent by weight.

The process according to the present invention has a feature that it allows a reaction to proceed smoothly under mild conditions. The reaction temperature can be chosen as appropriate according typically to the type(s) of the substrate(s) and the type of the target product and is typically about 10° C. to 200° C., preferably about 50° C. to 180° C., and especially preferably about 75° C. to 150° C. The reaction can be performed at normal atmospheric pressure or under a pressure (under a load). When the reaction is performed under a load, the pressure is generally about 0.1 to 10 MPa (e.g., about 0.15 to 8 MPa, and preferably about 0.5 to 8 MPa). The reaction time can be chosen as appropriate according to the reaction temperature and pressure within the range of typically about 10 minutes to 48 hours.

The reaction can be performed in the presence of, or in the circulation of, oxygen according to a common procedure or system such as batch system, semibatch system, or continuous system. The reaction is preferably performed in a fluidized bed system or fixed bed system.

After the completion of the reaction, a reaction product can be separated and purified according to a separation procedure such as filtration, concentration, distillation, extraction, crystallization, recrystallization, or column chromatography, or any combination of these separation procedures.

Recovery and Reuse of Transition Metal Compound

After the completion of the reaction, the transition metal compound supported on the solid superacid and used in the reaction can be easily recovered from the reaction mixture typically through a physical procedure such as filtration or centrifugal separation. The recovered transition metal compound supported on the solid superacid is reused without being treated or after subjected to washing and drying treatments. The washing treatment can be performed by washing the recovered catalyst several times (e.g., two or three times) with an appropriate solvent such as ethyl acetate.

The transition metal compound is used in the present invention as being supported on the solid superacid, is thereby resistant to elution or dissolution out even during organic synthesis reactions, and can be efficiently recovered by recovering the solid superacid. The recovered transition metal compound can show catalytic potency approximately equivalent to that of an unused transition metal compound and is significantly resistant to decrease in catalytic potency even after repeating use-recovery procedures multiple times, e.g., even after repeating use-regeneration procedures about ten times. Accordingly, the process for the production of an oxygen-containing organic compound according to the present invention can inexpensively provide oxygen-containing organic compounds which are useful in the chemical industry, because the process enables repeated recoveries and reuses of the transition metal compound which forms a large proportion of the production cost of such oxygen-containing organic compounds, and this significantly reduces the production cost.

EXAMPLES

The present invention will be illustrated in further detail with reference to several working examples below. It should be noted, however, that these examples are never construed to limit the scope of the present invention. Analyses of reaction products were performed typically through gas chromatography and high-performance liquid chromatography.

Preparation Example 1

In 10 mL of acetic acid was dissolved 250 mg of cobalt(II) acetate tetrahydrate, and then 2.5 g of a sulfated zirconia (supplied by Wako Pure Chemical Industries Ltd., as pellets) was suspended therein, followed by stirring at 100° C. for 16 hours. Of the support, portions which had been pulverized into powder during stirring were removed, and residual slightly purple pellets were recovered, washed with acetic acid and with ethyl ether, and thereby yielded a catalyst A. The prepared catalyst A was immersed in a concentrated nitric acid to elute cobalt metal from the catalyst A, and the resulting concentrated nitric acid solution containing the eluted cobalt metal was analyzed through atomic absorption spectrometry to find that the amount of the cobalt metal supported on the catalyst A was 1.6 percent by weight.

Preparation Example 2

In 10 mL of acetic acid were dissolved 250 mg of cobalt(II) acetate tetrahydrate and 250 mg of manganese(II) acetate tetrahydrate, and then 2.5 g of a sulfated zirconia (supplied by Wako Pure Chemical Industries Ltd., as pellets) was suspended therein, followed by stirring at 100° C. for 16 hours. Of the support, portions which had been pulverized into powder during stirring were removed, residual purple pellets were recovered, washed with acetic acid and with ethyl ether, and thereby yielded a catalyst B. The prepared catalyst B was immersed in a concentrated nitric acid to elute cobalt metal and manganese metal from the catalyst B, the resulting concentrated nitric acid solution containing the eluted cobalt metal and manganese metal was analyzed through atomic absorption spectrometry to find that the amounts of the cobalt metal and manganese metal supported on the catalyst B were 1.3 percent by weight and 1.3 percent by weight, respectively.

Preparation Example 3

In 10 mL of acetic acid was dissolved 250 mg of cobalt(II) acetate tetrahydrate, and then 2.5 g of a sulfated zirconia (supplied by Wako Pure Chemical Industries Ltd., as pellets) was suspended therein, followed by stirring at 100° C. for 16 hours. Of the support, portions which had been pulverized into powder during stirring were removed, and residual slightly purple pellets were recovered.

In 5 mL of acetic acid was dissolved 158 mg of zirconium (IV) (oxo)bis(acetylacetonate), and 1.33 g of the recovered pellets were suspended therein, followed by stirring at 100° C. for 14 hours. Of the support, portions which had been pulverized into powder during stirring were removed, residual pellets were recovered, washed with acetic acid and with ethyl ether, and thereby yielded a catalyst C. The prepared catalyst C was immersed in a concentrated nitric acid to elute cobalt metal from the catalyst C, the concentrated nitric acid solution containing the eluted cobalt metal was analyzed through atomic absorption spectrometry to find that the amount of the cobalt metal supported on the catalyst C was 1.6 percent by weight.

Example 1

In 3 mL of acetic acid was dissolved 300 mg of p-t-butyltoluene to give a solution, and the solution was further combined with 150 mg of the catalyst A and 33 mg of N-hydroxyphthalimide, followed by stirring at 100° C. in an oxygen atmosphere for 6 hours. The reaction mixture was analyzed through gas chromatography to find that p-t-butylbenzoic acid and p-t-butylbenzaldehyde were obtained in yields of 66.5% and 3.8%, respectively, with a conversion from p-t-butyltoluene of 82.2%. The catalyst A was separated from the reaction mixture through filtration, washed with ethyl acetate two times, dried at room temperature (25° C.) under reduced pressure, and recovered as a catalyst $A^1$. The cobalt ion concentration in the reaction mixture, from which the catalyst $A^1$ had been separated through filtration, was measured through atomic absorption spectrometry and was found to be 24 ppm.

Example 2

The procedure of Example 1 was repeated, except for using the catalyst $A^1$ obtained from Example 1 instead of the catalyst A, to give p-t-butylbenzoic acid in a yield of 65.9% and p-t-butylbenzaldehyde in a yield of 3.4%, with a conversion from p-t-butyltoluene of 85.1%.

By the procedure of Example 1, the catalyst $A^1$ was recovered as a catalyst $A^2$.

Example 3

The procedure of Example 1 was repeated, except for using the catalyst $A^2$ obtained from Example 2 instead of the catalyst A, to give p-t-butylbenzoic acid in a yield of 63.3% and p-t-butylbenzaldehyde in a yield of 3.6%, with a conversion from p-t-butyltoluene of 82.4%.

By the procedure of Example 1, the catalyst $A^2$ was recovered as a catalyst $A^3$.

Example 4

The procedure of Example 1 was repeated, except for using the catalyst $A^3$ obtained from Example 3 instead of the catalyst A, to give p-t-butylbenzoic acid in a yield of 59.2% and p-t-butylbenzaldehyde in a yield of 4.2%, with a conversion from p-t-butyltoluene of 81.5%.

By the procedure of Example 1, the catalyst $A^3$ was recovered as a catalyst $A^4$.

Example 5

The procedure of Example 1 was repeated, except for using the catalyst $A^4$ obtained from Example 4 instead of the catalyst A, to give p-t-butylbenzoic acid in a yield of 65.0% and p-t-butylbenzaldehyde in a yield of 3.8%, with a conversion from p-t-butyltoluene of 82.4%.

By the procedure of Example 1, the catalyst $A^4$ was recovered as a catalyst $A^5$.

Example 6

The procedure of Example 1 was repeated, except for using the catalyst $A^5$ obtained from Example 5 instead of the catalyst A, to give p-t-butylbenzoic acid in a yield of 52.7% and p-t-butylbenzaldehyde in a yield of 4.5%, with a conversion from p-t-butyltoluene of 77.6%.

By the procedure of Example 1, the catalyst $A^5$ was recovered as a catalyst $A^6$.

Example 7

The procedure of Example 1 was repeated, except for using the catalyst $A^6$ obtained from Example 6 instead of the catalyst A, to give p-t-butylbenzoic acid in a yield of 48.3% and p-t-butylbenzaldehyde in a yield of 4.3%, with a conversion from p-t-butyltoluene of 75.6%.

By the procedure of Example 1, the catalyst $A^6$ was recovered as a catalyst $A^7$.

Example 8

The procedure of Example 1 was repeated, except for using the catalyst $A^7$ obtained from Example 7 instead of the catalyst A, to give p-t-butylbenzoic acid in a yield of 56.8% and p-t-butylbenzaldehyde in a yield of 4.7%, with a conversion from p-t-butyltoluene of 76.6%.

By the procedure of Example 1, the catalyst $A^7$ was recovered as a catalyst $A^8$.

Example 9

The procedure of Example 1 was repeated, except for using the catalyst $A^8$ obtained from Example 8 instead of the catalyst A, to give p-t-butylbenzoic acid in a yield of 64.5% and p-t-butylbenzaldehyde in a yield of 5.3%, with a conversion from p-t-butyltoluene of 75.8%.

By the procedure of Example 1, the catalyst $A^8$ was recovered as a catalyst $A^9$.

Example 10

The procedure of Example 1 was repeated, except for using the catalyst $A^9$ obtained from Example 9 instead of the catalyst A, to give p-t-butylbenzoic acid in a yield of 48.7% and p-t-butylbenzaldehyde in a yield of 4.8%, with a conversion from p-t-butyltoluene of 75.5%.

By the procedure of Example 1, the catalyst $A^9$ was recovered as a catalyst $A^{10}$.

Example 11

In 3 mL of acetic acid was dissolved 300 mg of p-t-butyltoluene to give a solution, and the solution was further combined with 150 mg of the catalyst B and 33 mg of N-hydroxyphthalimide, followed by stirring at 100° C. in an oxygen atmosphere for 6 hours. The reaction mixture was analyzed through gas chromatography to find that p-t-butylbenzoic acid and p-t-butylbenzaldehyde were obtained in yields of 55.6% and 4.0%, respectively, with a conversion from p-t-butyltoluene of 76.5%. The catalyst B was separated from the reaction mixture through filtration, washed with ethyl acetate two times, dried at room temperature (25° C.) under reduced pressure, and thereby recovered as a catalyst $B^1$. The cobalt ion concentration and manganese ion concentration in the reaction mixture, from which the catalyst $B^1$ had been separated through filtration, were measured through atomic absorption spectrometry and found to be 21 ppm and 24 ppm, respectively.

Example 12

The procedure of Example 11 was repeated, except for using the catalyst $B^1$ obtained from Example 11 instead of the catalyst B, to give p-t-butylbenzoic acid in a yield of 76.1% and p-t-butylbenzaldehyde in a yield of 3.0%, with a conversion from p-t-butyltoluene of 86.7%.

By the procedure of Example 11, the catalyst $B^1$ was recovered as a catalyst $B^2$.

Example 13

The procedure of Example 11 was repeated, except for using the catalyst $B^2$ obtained from Example 12 instead of the catalyst B, to give p-t-butylbenzoic acid in a yield of 61.4% and p-t-butylbenzaldehyde in a yield of 3.0%, with a conversion from p-t-butyltoluene of 86.7%.

By the procedure of Example 11, the catalyst $B^2$ was recovered as a catalyst $B^3$.

Example 14

The procedure of Example 11 was repeated, except for using the catalyst $B^3$ obtained from Example 13 instead of the catalyst B, to give p-t-butylbenzoic acid in a yield of 61.8% and p-t-butylbenzaldehyde in a yield of 3.0%, with a conversion from p-t-butyltoluene of 85.7%.

By the procedure of Example 11, the catalyst $B^3$ was recovered as a catalyst $B^4$.

Example 15

The procedure of Example 11 was repeated, except for using the catalyst $B^4$ obtained from Example 14 instead of the catalyst B, to give p-t-butylbenzoic acid in a yield of 70.1% and p-t-butylbenzaldehyde in a yield of 3.6%, with a conversion from p-t-butyltoluene of 84.7%.

By the procedure of Example 11, the catalyst $B^4$ was recovered as a catalyst $B^5$.

Example 16

The procedure of Example 11 was repeated, except for using the catalyst $B^5$ obtained from Example 15 instead of the catalyst B, to give p-t-butylbenzoic acid in a yield of 75.6% and p-t-butylbenzaldehyde in a yield of 3.9%, with a conversion from p-t-butyltoluene of 83.2%.

By the procedure of Example 11, the catalyst $B^5$ was recovered as a catalyst $B^6$.

Example 17

The procedure of Example 11 was repeated, except for using the catalyst $B^6$ obtained from Example 16 instead of the catalyst B, to give p-t-butylbenzoic acid in a yield of 60.5% and p-t-butylbenzaldehyde in a yield of 3.2%, with a conversion from p-t-butyltoluene of 85.5%.

By the procedure of Example 11, the catalyst $B^6$ was recovered as a catalyst $B^7$.

Example 18

The procedure of Example 11 was repeated, except for using the catalyst $B^7$ obtained from Example 17 instead of the catalyst B, to give p-t-butylbenzoic acid in a yield of 68.2% and p-t-butylbenzaldehyde in a yield of 4.5%, with a conversion from p-t-butyltoluene of 80.8%.

By the procedure of Example 11, the catalyst $B^7$ was recovered as a catalyst $B^8$.

Example 19

The procedure of Example 11 was repeated, except for using the catalyst $B^8$ obtained from Example 18 instead of the catalyst B, to give p-t-butylbenzoic acid in a yield of 53.9% and p-t-butylbenzaldehyde in a yield of 4.6%, with a conversion from p-t-butyltoluene of 78.9%.

By the procedure of Example 11, the catalyst $B^8$ was recovered as a catalyst $B^9$.

Example 20

The procedure of Example 11 was repeated, except for using the catalyst $B^9$ obtained from Example 19 instead of the catalyst B, to give p-t-butylbenzoic acid in a yield of 55.7% and p-t-butylbenzaldehyde in a yield of 4.4%, with a conversion from p-t-butyltoluene of 80.1%.

Comparative Example 1

In 3 mL of acetic acid was dissolved 300 mg of p-t-butyltoluene to give a solution, and the solution was combined with 150 mg of pellets of a sulfated zirconia and 33 mg of N-hydroxyphthalimide, followed by stirring at 100° C. in an oxygen atmosphere for 6 hours. The reaction mixture was analyzed through gas chromatography to find that a conversion from p-t-butyltoluene was 0%.

Comparative Example 2

In 3 mL of acetic acid was dissolved 300 mg of p-t-butyltoluene to give a solution, and the solution was combined with 10 mg of cobalt(II) acetate tetrahydrate and 33 mg of N-hydroxyphthalimide, followed by stirring at 100° C. in an oxygen atmosphere for 6 hours. The reaction mixture was analyzed through gas chromatography to find that p-t-butylbenzoic acid was produced in a yield of 93.5%, with a conversion from p-t-butyltoluene of 100%. The cobalt ion concentration in the reaction mixture was measured through atomic absorption spectrometry and found to be 800 ppm.

Example 21

The procedure of Example 11 was repeated, except for using 286 mg of adamantane instead of 300 mg of p-t-butyltoluene, to give 1-adamantanol in a yield of 12.0%, 2-adamantanone in a yield of 8.0%, and adamantane-1,3-diol in a yield of 24%, with a conversion from adamantane of 98%.

Example 22

In 3 mL of acetic acid was dissolved 249 mg of 2-phenylethanol to give a solution, and the solution was combined with 150 mg of the catalyst B and 32 mg of N-hydroxyphthalimide, followed by stirring at 70° C. in an oxygen atmosphere at normal atmospheric pressure for 4 hours. The reaction mixture was analyzed through gas chromatography to find that acetophenone was produced in a yield of 100%, with a conversion from 2-phenylethanol of 100%.

The catalyst B was separated from the reaction mixture through filtration, washed with ethyl acetate two times, dried at room temperature (25° C.) under reduced pressure, and thereby recovered as a catalyst $B^{10}$.

Example 23

In 3 mL of acetic acid was dissolved 375 mg of 1-undecanol to give a solution, and the solution was combined with 150 mg of the catalyst $B^{10}$ obtained from Example 22 and 32 mg of N-hydroxyphthalimide, followed by stirring at 100° C. in an oxygen atmosphere at normal atmospheric pressure for 4 hours. The reaction mixture was analyzed through gas chromatography to find that undecanoic acid was produced in a yield of 22% with a conversion from 1-undecanol of 44%.

Example 24

In 3 mL of acetic acid was dissolved 315 mg of p-t-butyltoluene to give a solution, and the solution was combined with 156 mg of the catalyst C and 42 mg of hexahydro-1,3,5-trihydroxy-1,3,5-triazine-2,4,6-trione (hereinafter also referred to as "THICA"), followed by stirring at 100° C. in an oxygen atmosphere for 6 hours. The reaction mixture was analyzed through gas chromatography to find that p-t-butylbenzoic acid and p-t-butylbenzaldehyde were produced in yields of 84.5% and 1.4%, respectively, with a conversion from p-t-butyltoluene of 99.7%. The catalyst C was separated from the reaction mixture through filtration, washed with ethyl acetate two times, dried at room temperature (25° C.) under reduced pressure, and thereby recovered as a catalyst $C^1$.

Example 25

The procedure of Example 24 was repeated, except for using the catalyst $C^1$ obtained from Example 24 instead of the catalyst C and using THICA in an amount of 23 mg, to give p-t-butylbenzoic acid in a yield of 4.0% and p-t-butylbenzaldehyde in a yield of 8.0%, with a conversion from p-t-butyltoluene of 15.5%.

By the procedure of Example 24, the catalyst C¹ was recovered as a catalyst C².

Example 26

The procedure of Example 25 was repeated, except for using the catalyst C² obtained from Example 25 instead of the catalyst C¹, to give p-t-butylbenzoic acid in a yield of 28.1% and p-t-butylbenzaldehyde in a yield of 10.0%, with a conversion from p-t-butyltoluene of 44.8%.

By the procedure of Example 24, the catalyst C² was recovered as a catalyst C³.

Example 27

The procedure of Example 25 was repeated, except for using the catalyst C³ obtained from Example 26 instead of the catalyst C¹ and for performing the reaction for 16 hours, to give p-t-butylbenzoic acid in a yield of 84.3% and p-t-butylbenzaldehyde in a yield of 0.9%, with a conversion from p-t-butyltoluene of 98.9%.

Industrial Applicability

The present invention can significantly reduce the production cost of oxygen-containing organic compounds and can inexpensively provide such oxygen-containing organic compounds which are useful in the chemical industry, because the present invention enables the recovery and reuse of transition metal compounds, which form a large proportion of the production cost, and allows the recovered transition metal compounds to be resistant to reduction in catalytic potency even after repeating use-recovery procedures multiple times.

The invention claimed is:

1. A process for the production of an oxygen-containing organic compound, the process comprising the step of oxidizing an organic compound with molecular oxygen in a liquid phase in the presence both of a nitrogen-containing cyclic compound and of a catalyst including a solid superacid and a transition metal compound supported on the solid superacid, to give the oxygen-containing organic compound, the nitrogen-containing cyclic compound containing, as a ring constituent, a skeleton represented by following Formula (1):

[Chemical Formula 1]

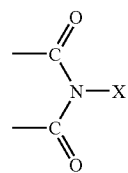

(1)

wherein X represents an —OR group, wherein R represents a hydrogen atom or a hydroxyl-protecting group.

2. The process for the production of an oxygen-containing organic compound of claim 1, wherein the solid superacid is a sulfated zirconia.

3. The process for the production of an oxygen-containing organic compound of claim 1 or 2, wherein the transition metal compound is a cobalt compound and/or a manganese compound.

4. The process of claim 1 for the production of p-tertiary-butylbenzoic acid, wherein said organic compound is p-tertiary-butyltoluene and said nitrogen-containing cyclic compound is N-hydroxyphthalimide.

5. The process of claim 1, wherein said organic compound is a member selected from the group consisting of para-tertiary-butyltoluene, adamantane, 2-phenylethanol, and 1-undecanol.

6. The process of claim 1, wherein said organic compound is a member selected from the group consisting of hydrocarbons having a methine carbon atom, aromatic hydrocarbons having a methyl group or methylene group adjacent to an aromatic ring, and nonaromatic cyclic hydrocarbons.

7. The process of claim 1, wherein said organic compound is a member selected from the group consisting of
  (A1) heteroatom-containing compounds having a carbon-hydrogen bond at an adjacent position to the heteroatom,
  (A2) compounds having a carbon-heteroatom double bond,
  (A3) compounds having a methine carbon atom,
  (A4) compounds having a carbon-hydrogen bond at an adjacent position to an unsaturated bond,
  (A5) non-aromatic compounds,
  (A6) conjugated compounds,
  (A7) aromatic compounds,
  (A8) linear alkanes, and
  (A9) olefins.

* * * * *